United States Patent [19]

Ember

[11] Patent Number: 5,309,915
[45] Date of Patent: May 10, 1994

[54] APPARATUS FOR LOCATING VEINS AND ARTERIES

[75] Inventor: Charles T. Ember, Marion County, Ind.

[73] Assignee: MTE, Inc., Indianapolis, Ind.

[21] Appl. No.: 73,151

[22] Filed: Jun. 7, 1993

[51] Int. Cl.$^5$ ............................................... A61B 8/06
[52] U.S. Cl. ................................................ 128/661.07
[58] Field of Search ...................... 128/662.03–662.06, 128/661.07–661.09

[56] References Cited

U.S. PATENT DOCUMENTS

| | | | |
|---|---|---|---|
| 4,086,916 | 5/1978 | Freeman et al. | 128/662.04 X |
| 4,413,629 | 11/1983 | Durley | 128/662.04 X |
| 4,986,276 | 1/1991 | Wright | 128/662.04 |
| 5,046,364 | 9/1991 | Stasuk et al. | 73/623 |
| 5,080,101 | 1/1992 | Dory | 128/660.03 |
| 5,080,103 | 1/1992 | Olivier | 128/662.05 |
| 5,080,104 | 1/1992 | Marks et al. | 128/662.05 |
| 5,103,825 | 4/1992 | Hokanson | 128/661.07 |
| 5,131,395 | 7/1992 | Gehlbach | 128/662.05 |
| 5,158,088 | 10/1992 | Nelson et al. | 128/662.05 |
| 5,167,630 | 12/1992 | Paul | 604/179 |

*Primary Examiner*—Francis Jaworski
*Attorney, Agent, or Firm*—Jack Schuman

[57] ABSTRACT

Apparatus for locating blood vessels in a live human body is self-contained, compact, non-invasive, and fully movable about the body.

Within a housing of the general size and shape of a pen and having a distal end and a proximal end, solid state electrical circuitry generates high-frequency electrical signals producing ultrasonic signals directed ahead of the distal end toward a narrow area of a body, receives the ultrasonic echoes of the ultrasonic signals and generates high-frequency electrical signals in response to said echoes, mixes both high-frequency electrical signals and amplifies the resulting differentials to produce beats, the amplitudes of which will vary if a Doppler effect due to the pulsating flow of blood through a vein or artery is detected. These amplified differential signals or beats are used to drive a miniature loudspeaker at the proximal end of the housing.

10 Claims, 3 Drawing Sheets

APPARATUS FOR LOCATING VEINS AND ARTERIES

BACKGROUND OF THE INVENTION

1. Field of the Invention

This invention relates, broadly speaking, to an improved device for locating flowing fluids such as blood in a body.

More particularly, this invention relates to a totally self-contained, non-invasive, freely movable device for locating veins and arteries in a live human body.

(2) Description of the Prior Art

Various devices for locating veins and arteries in a live human body are known.

Some of these devices are based upon the use of ultrasonic signals and the Doppler effect for locating veins and arteries in the human body by detecting the flow of blood therethrough, reference being made to U.S. Pat. Nos. 5,167,630, 5,131,395, 5,103,825, 5,080,104, 5,080,103 and 4,887,606.

None of these prior art devices are totally self-contained, non-invasive and freely movable, the combination of all of said properties being found only in the present invention.

SUMMARY OF THE INVENTION

One of the objects of this invention is to provide an improved device for locating flowing fluids such as blood in a live human body.

Another of the objects of this invention is to provide an improved, totally self-contained, non-invasive, freely movable device employing ultrasonics and the Doppler effect, for locating veins and arteries in a live human body by detecting the flow of blood therethrough.

A further object of this invention is to provide a compact, relatively inexpensive and reliable device for locating veins and arteries in a live human body.

Other and further objects of this invention will become apparent by reference to this specification, the accompanying drawings and the appended claims.

Briefly, the foregoing objects are attained by providing, totally within a housing of the general size and shape of a pen, a compact source of power and solid state electronics adapted (1) to generate high-frequency electrical signals producing ultrasonic signals directed toward a narrow area of an immediately adjacent human body, (2) to detect ultrasonic echoes and to generate high-frequency electrical signals in response to said echoes, and (3) to mix both high frequency electrical signals and amplify the resulting differentials to produce beats, the amplitudes of which will vary if a Doppler effect due to the pulsating flow of blood through a vein or artery is detected. These amplified differential signals or beats are used to drive a miniature loudspeaker in the housing. Alternatively, this signal can be used to drive headphones or a display device.

DESCRIPTION OF THE DRAWINGS

Referring now to the drawings, in which like numerals represent like parts in the several views.

DESCRIPTION OF THE PREFERRED EMBODIMENT

The device of the present invention consists of electronic circuitry mounted within a tubular housing 1 of the general size and shape of a conventional fountain pen.

The electronic circuitry is compact, and is adapted to project ultrasonic signals from one end, the distal end, thereof toward a narrow area of a live human body 2 having a vein or artery 3 which is to be located by the device, and is further adapted to detect ultrasonic echoes from the human body 2 of said ultrasonic signals.

High-frequency electrical signals produced by an electrical oscillator within housing 1 and which produce the ultrasonic signals are mixed with electrical signals generated by the ultrasonic echoes in one portion of the electronic circuitry, to produce differential or beat signals, the amplitudes of which are responsive to the Doppler effect created by a surging or pulsating flow of liquid, in this case blood, through the vein or artery 3.

When such Doppler effect is sensed by the device, the fluctuations in amplitude of the beat signals are perceived by the user of the device through a speaker. In this manner, a vein or artery 3 can easily and noninvasively be detected by the device which is unencumbered by attachments to the human body 2 or peripheral apparatus and which therefore is freely movable about the human body 2.

Figure 1:
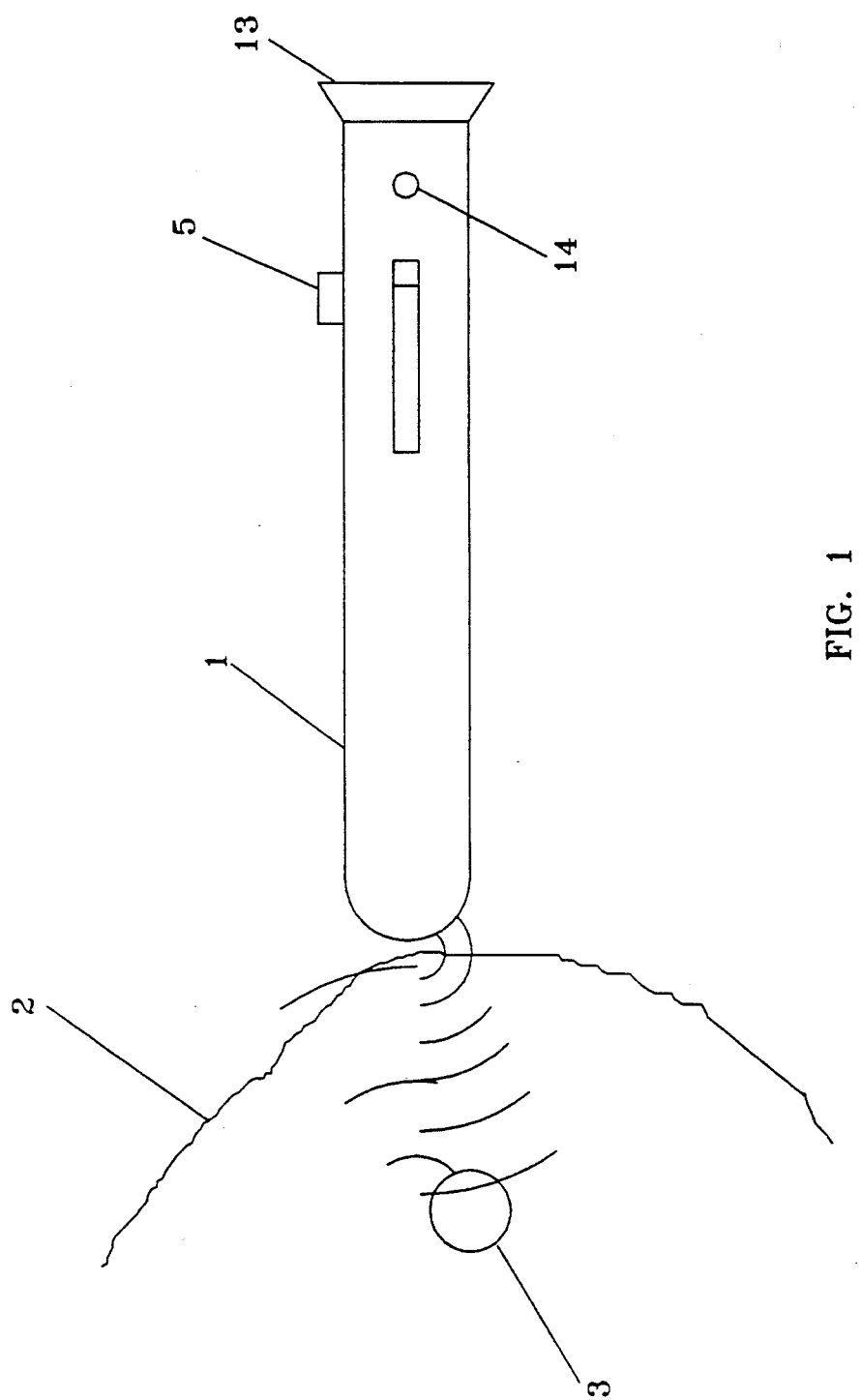
FIG. 1 represents a view in side elevation of the present invention in use adjacent a live human body, showing diagrammatically ultrasonic waves generated by the present invention and directed toward a vein or artery in the human body and ultrasonic echoes from the vein or artery and directed toward and received by the present invention.
Figure 2A:
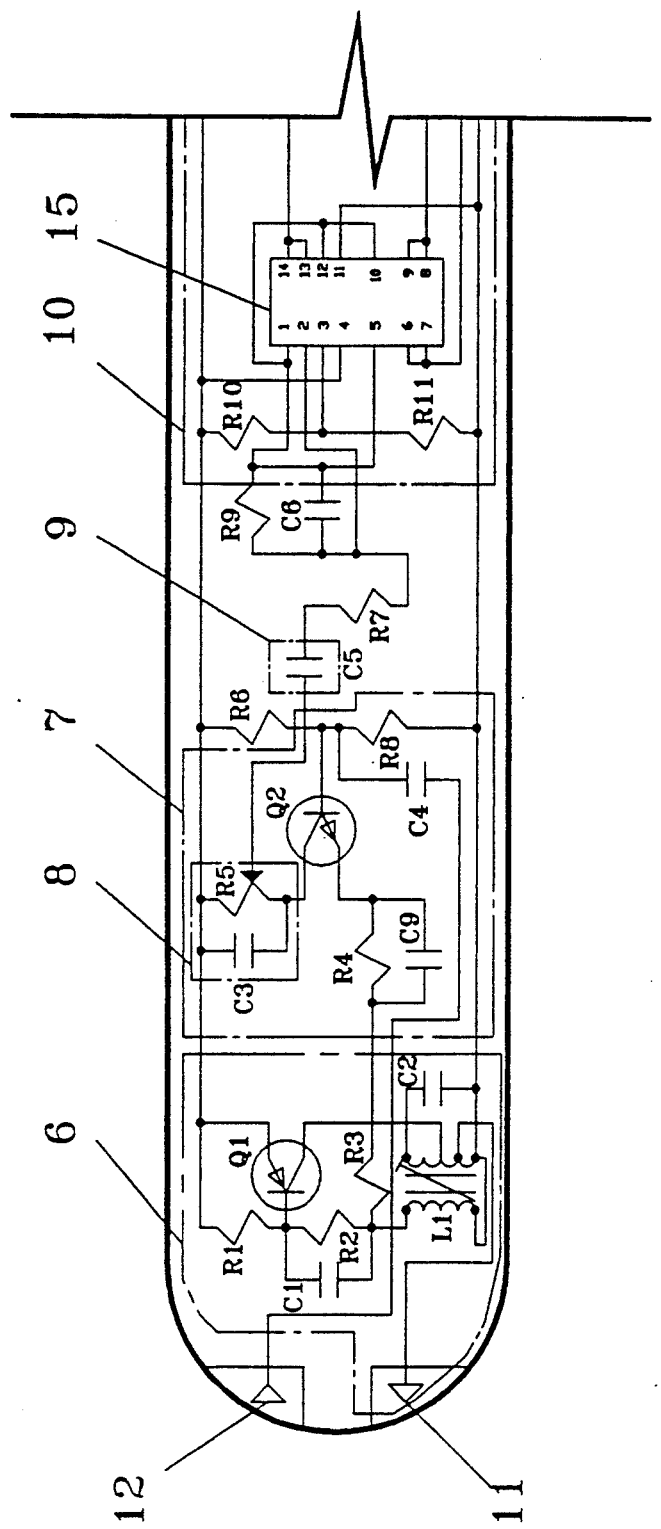
FIG. 2A represents an enlarged longitudinal medial section, partially diagrammatic, of the distal half of the present invention, showing the circuitry mounted therein, the vertical line at the right representing the left end of FIG. 2B.
Figure 2B:
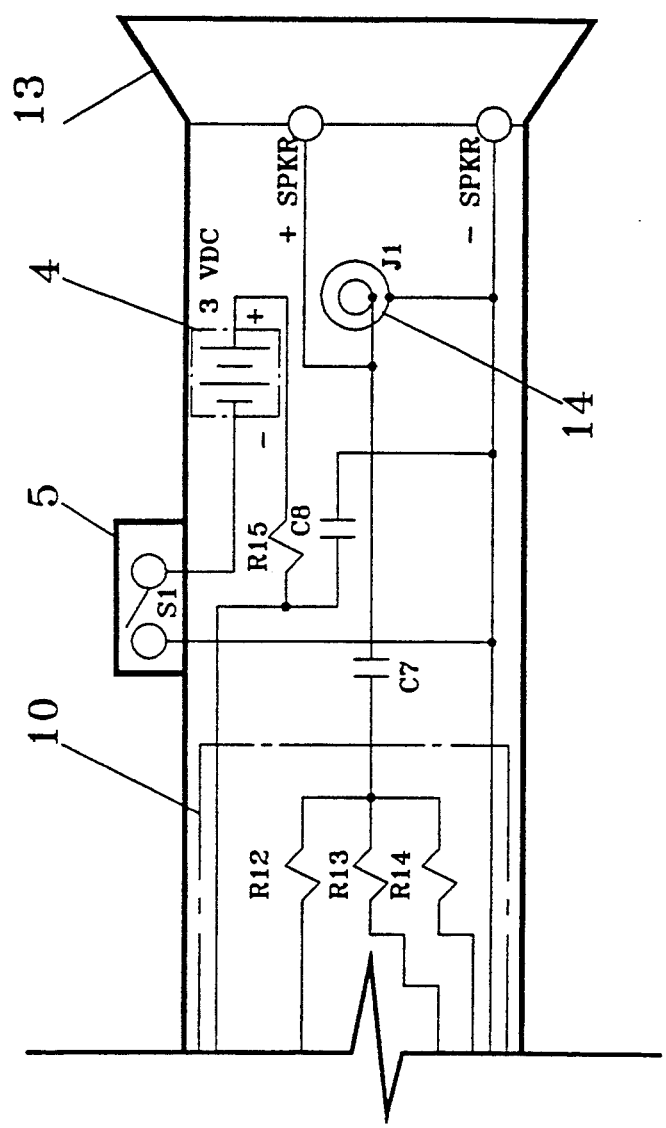
FIG. 2B represents an enlarged longitudinal medial section, partially diagrammatic, of the proximal half of the present invention, showing the circuitry mounted therein, the vertical line at the left representing the right end of FIG. 2A.

The electronic circuitry consists of several functional sections, each of which is well known in the art and each of which comprises standard components which are indicated in FIGS. 2A and 2B by standard symbols. Major functional sections are shown enclosed by phantom borders in FIGS. 2A and 2B for ease of identification and comprehension by those to whom this specification is addressed.

Power supply 4, preferably a 3 volt battery, is connected through switch 5 to oscillator section 6 which produces high-frequency electrical signals, mixer section 7 including a low pass filter and gain control 8, decoupling capacitor 9, and inverting amplifier section 10, as shown and all in a manner known to those familiar with this art.

Part of the high-frequency electrical output of oscillator section 6 is communicated to a conventional ultrasonic transducer 11 which generates and projects ultrasonic signals toward a narrow area of the human body 2. Part of the high-frequency electrical output of oscillator section 6 is communicated to mixer section 7.

Conventional ultrasonic transducer 12 detects ultrasonic echoes from human body 2, and generates high-frequency electrical signals in response thereto, which high-frequency electrical signals are communicated to mixer section 7.

The high-frequency electrical signals from oscillator section 6 and the high-frequency electrical signals from ultrasonic transducer 12 are combined in mixer section 7 to produce differential or beat signals.

The differential or beat signals are then communicated to inverting amplifier section 10, which includes a filter and a gain stage, to produce signals which drive speaker 13.

Tap or socket 14 is provided in the electrical circuitry as shown, and is adapted to receive a plug connected to an auxiliary or external speaker or to a display device (not shown), whereby the output of inverting amplifier section 10 can drive said auxiliary or external speaker or be displayed on said display device.

Element 15 in inverting amplifier section 10 is a conventional solid state 2N6484N amplifying circuit.

Preferably transistor Q1 is of type 2N4403.

Preferably, transistor Q2 is of type 2N4401.

Preferably, oscillator L1 in oscillator section 10 produces an electrical output signal of 2–4 µH frequency.

The preferred values for the several capacitors and resistors in the electrical circuit are:

```
R1–10k ohms
R2–33k ohms
R3–100 ohms
R4–330 ohms
R5–1k ohms
R6–20k ohms
R7–10k ohms
R8–10k ohms
R9–1 meg ohm
R10–100k ohms
R11–100k ohms
R12–47 ohms
R13–47 ohms
R14–47 ohms
R15–0.51 ohms (fusible)
C1–330 µF
C2–330 µF
C3–1 nF
C4–330 pF
C5–0.1. µF
C6–27 pF
C7–47 µF
C8–47 µF
C9–1 nF
```

For convenience of the user, a pocket clip 16 is secured to housing 1.

The operation of the device will now be described.

Switch 5 is moved to the "on" position to complete the electrical circuit, causing ultrasonic signals to be generated by ultrasonic transducer 11 and projected forwardly of the distal end of the device.

The device is then placed in contact with human body 2 and freely moved around the surface of said human body. In the absence of the distal end of the device being in proximity with a vein or artery 3 carrying a pulsating flow of blood, there will be no Doppler effect to sense, and no differential or beat signal will be produced by mixer section 7.

When, however, ultrasonic signals from ultrasonic transducer 11 reach close proximity to a vein or artery 3, the Doppler effect created by blood surging in a pulsating manner through said vein or artery 3 will periodically change the frequency of the ultrasonic echoes, thus causing differential or beat signals to be produced, and these can be perceived by listening to the speaker 13.

It will be understood that the velocity of blood through a vein or artery 3 is not constant, and is in fact a continuous series of surges or pulses caused by the pumping action of the heart. Thus, the Doppler effect of the surging or pulsating flow of blood will not be constant, and this is why beat signals of varying amplitude result. In this manner, medical personnel can locate with great precision the vein or artery 3 in a human body.

In the preferred embodiment, the focus of the transducers 11 and 12 lie between 1 and 2 centimeters forward of the distal end of the device. Maximum sensitivity of the device is 0.5 to 2 centimeters from the distal end thereof.

This device is particularly useful in situations where veins are difficult to locate visually or by palpation, and in situations where a vein or artery must be located rapidly. Because the device is non-invasive, and is accurate, the patient will undergo considerably less pain.

Trained medical personnel, with practice, will be able to distinguish blood flow through a vein from blood flow through an artery.

The device can also be used to locate a surging or pulsating flow of liquid through conduits in non-medical applications.

The foregoing specification is illustrative of the principles of the invention. Since modifications and changes which do not depart from the spirit of the invention may readily occur to those skilled in the art to which this invention pertains, this invention should not be considered as limited to the exact apparatus shown and described herein, and the appended claims should be construed as covering suitable modifications and equivalents.

I claim:

1. Apparatus for locating a visually inaccessible pulsating flow of fluid within a body, said apparatus being self-contained, compact, non-invasive and freely movable about the body, said apparatus comprising:

(a) a housing having a distal end and a proximal end, (b) a source of electrical power mounted within said housing, (c) an electrical oscillator mounted within said housing and connected to said source of electrical power, said electrical oscillator being adapted to produce high-frequency electrical signals, (d) a first ultrasonic transducer mounted within said housing closely adjacent the distal end thereof and connected to said electrical oscillator, said first ultrasonic transducer being adapted to produce and project ultrasonic signals toward a narrow area of said body in response to the high-frequency electrical signals received from said electrical oscillator, (e) a second ultrasonic transducer mounted within said housing closely adjacent the distal end thereof and adapted to detect ultrasonic echoes from said body and to generate high-frequency electrical signals in response to said ultrasonic echoes, (f) means connected to said electrical oscillator and adapted to receive electrical signals from said electrical oscillator of the same high frequency as received by said first ultrasonic transducer from said electrical oscillator, said means also being connected to said second ultrasonic transducer and adapted to receive high-frequency electrical signals generated by said second ultrasonic transducer, said means mixing both of said high-frequency electrical signals to produce a differential signal, (g) a speaker mounted adjacent the proximal end of said housing and connected to said means and adapted to receive said differential signal and produce an audible output signal in response thereto, (h) whereby, upon the distal end of said housing becoming proximate to said pulsating flow of fluid within said body, the speaker will generate an audible signal indicating the presence of said pulsating flow of fluid.

2. Apparatus as in claim 1, further comprising:

(i) switch means interposed between said source of electrical power and said electrical oscillator.

3. Apparatus as in claim 1, wherein said means comprises:

(i) mixer circuitry adapted to combine the said high-frequency electrical signals, (j) an inverting amplifier connected to said mixer circuitry and receiving the said combined high-frequency electrical signals, said inverting amplifier being adapted to invert said combined electrical signals and amplify the resulting electrical signal sufficiently to drive said speaker.

4. Apparatus as in claim 1, wherein said housing is elongated and tubular in cross-section.

5. Apparatus as in claim 1, wherein the focus of said first and second ultrasonic transducers lies between 1–2 centimeters forward of the distal end of said housing.

6. Apparatus for locating in a live human body blood vessels through which flows a pulsating stream of blood, said apparatus being self-contained, compact, non-invasive and freely movable about the body, said apparatus comprising:

(a) a housing having a distal end and a proximal end, (b) a source of electrical power mounted within said housing, (c) an electrical oscillator mounted within said housing and connected to said source of electrical power, said electrical apparatus being adapted to produce high-frequency electrical signals, (d) a first ultrasonic transducer mounted within said housing closely adjacent the distal end thereof and connected to said electrical oscillator, said first ultrasonic transducer being adapted to produce and project ultrasonic signals towards a narrow area of said body in response to the high-frequency electrical signals received from said electrical oscillator, (e) a second ultrasonic transducer mounted within said housing closely adjacent the distal end thereof and adapted to detect ultrasonic echoes from said body and to generate high-frequency electrical signals in response to said ultrasonic echoes, (f) means connected to said electrical oscillator and adapted to receive electrical signals from said electrical oscillator of the same high frequency as received by said first ultrasonic transducer from said electrical oscillator, said means also being connected to said second ultrasonic transducer and adapted to receive high-frequency electrical signals generated by said second ultrasonic transducer, said means mixing both of said high-frequency electrical signals to produce a differential signal, (g) a speaker mounted adjacent the proximal end of said housing and connected to said means and adapted to receive said differential signal and produce an audible signal in response thereto;

(h) whereby, upon the distal end of said housing becoming proximate to said blood vessel, the speaker will generate an audible signal indicating the location of said blood vessel.

7. Apparatus as in claim 6, further comprising:

(i) switch means interposed between said source of electrical power and said electrical oscillator.

8. Apparatus as in claim 6, wherein said means comprises:

(i) mixer circuitry adapted to combined the said high-frequency electrical signals, (j) an inverting amplifier connected to said mixer circuitry and receiving the said combined high-frequency electrical signals, said inverting amplifier being adapted to invert said combined electrical signals and amplify the resulting electrical signal sufficiently to drive said speaker.

9. Apparatus as in claim 6, wherein said housing is elongated and tubular in cross-section.

10. Apparatus as in claim 6, wherein the focus of said first and second ultrasonic transducers lies between 1–2 centimeters forward of the distal end of said housing.

* * * * *